United States Patent [19]

Paul et al.

[11] Patent Number: 4,861,381

[45] Date of Patent: Aug. 29, 1989

[54] PROCESS FOR THE ENZYMATIC PREPARATION FROM SUCROSE OF A MIXTURE OF SUGARS HAVING A HIGH CONTENT OF ISOMALTOSE, AND PRODUCTS OBTAINED

[75] Inventors: Francois B. Paul, Saint-Orens-De Gammeville; Pierre F. Monsan, Mondonville; Magali M. C. Remaud, Ramonville; Vincent P. Pelenc, Toulouse, all of France

[73] Assignee: Sucre Recherches et Developpements, France

[21] Appl. No.: 68,940

[22] Filed: Jul. 1, 1987

[30] Foreign Application Priority Data

Jul. 9, 1986 [FR] France ................................ 86 09989

[51] Int. Cl.[4] .......................... C12N 9/10; C12N 9/46; C13K 7/00; C13K 1/00
[52] U.S. Cl. ..................................... 127/41; 127/46.1; 127/46.2; 435/193; 435/211; 426/658
[58] Field of Search .................... 127/46.1, 46.2, 46.3, 127/41; 435/193, 211; 426/658

[56] References Cited

U.S. PATENT DOCUMENTS 2,742,365 4/1956 Corman et al. ..................... 435/211

OTHER PUBLICATIONS

Karl L. Smiley et al., "A Simplified Method for Preparing Linear Isomalto-Oligosaccharides", *Carbohydrate Research*, 108 (1982) pp. 279–283.
Chemical Abstracts, vol. 99, No. 19, Nov. 7, 1983, p. 488, Resume No. 156809a, Columbus, Ohio.

*Primary Examiner*—H. M. S. Sneed
*Assistant Examiner*—Chung K. Pak
*Attorney, Agent, or Firm*—Stevens, Davis, Miller & Mosher

[57] ABSTRACT

The invention relates to the field of biotechnology.

It relates to a process for preparing a syrup, the dry extract of which includes a high content of isomaltose, which comprises treating an aqueous solution of sucrose with a mixture of the enzymes dextransucrase and dextranase at a temperature of 0° to 50° C. and at a pH in the range from 4.5 to 7, so as to obtain an aqueous syrup containing fructose, isomaltose, glucose and, possibly, isomaltotriose as the main constituents.

The syrup obtained is a useful intermediate for the synthesis, in particular, of isomaltitol.

10 Claims, No Drawings

PROCESS FOR THE ENZYMATIC PREPARATION FROM SUCROSE OF A MIXTURE OF SUGARS HAVING A HIGH CONTENT OF ISOMALTOSE, AND PRODUCTS OBTAINED

The invention relates to a process for the enzymatic preparation of a syrup having a high content of isomaltose, as well as the syrup obtained.

Isomaltose is an intermediate product which is of value for the preparation of isomaltitol (or 6-O-α-D-glucopyranosyl-D-sorbitol) by catalytic hydrogenation. Isomaltitol possesses substantial sweetening power, is of low calorific value, is not cariogenic and can hence represent an advantageous substitute for sugar.

In addition, isomaltose, which consists of a dimer of glucose, possesses a (1→6) glucoside bond which is relatively stable and is a potential substrate for transesterifications, for the purpose of producing fats of low calorific value, for example.

Hitherto, isomaltose has been prepared by chemical or enzymatic treatment of various substrates, or by chemical or enzymatic hydrolysis of the dextran produced by the lactic bacterium *Leuconostoc mesenteroides* NRRL B 512 F, followed by stages of fractionation of the solutions obtained, by passing the latter through very high (10-15 meters) columns of strongly acidic cationic resin at relatively high temperature (45°-85° C.), for example as described in U.S.-A-4,521,252. Syrups are thereby obtained, the dry extract of which contains more than 40% of isomaltose, and this can be still further purified at the cost of additional operations. These processes are complicated and demand a large purification installation for their implementation.

The present invention is directed towards the provision of a simple process for the synthesis of a syrup having a high content of isomaltose starting with sucrose, by treatment of the latter using a novel combination of two enzymes.

More especially, the invention relates to a process for preparing a syrup, the dry extract of which includes a high content of isomaltose, which comprises—treating an aqueous solution of sucrose with a mixture of the enzymes dextransucrase (EC: 2.4.1.5) and dextranase (EC: 3.2.1.11 and 3.2.1.94), at a temperature of 0° to 50° C. and at a pH in the range from 4.5 to 7, so as to obtain an aqueous syrup containing isomaltose, fructose, glucose and, possibly, isomaltotriose as the main constituents.

The enzymatic reaction can be conducted discontinuously (batchwise) or continuously (reactor containing immobilized enzymes). Free or immobilized enzymes may be used without discrimination, or only one of the two enzymes may be immobilized. A complete conversion of the sucrose can be obtained when the reaction time is sufficient. The latter will be shortened by the use of a larger amount of enzymes and a higher reaction temperature. As a guide, reaction times of between 1 and 200 hours approximately, and preferably from 20 to 80 hours, may be used for a discontinuous method of operation.

The reaction may be described as follows: dextransucrase polymerizes the glucosyl residue of the sucrose and liberates fructose into the reaction medium. Dextranase, which specifically produces isomaltose, prevents the formation of the polymer (dextran) by hydrolysing the α1→6 glucoside bond as it is formed by the dextransucrase. The medium hence becomes enriched in isomaltose as the sucrose is converted. The simultaneous action of these two enzymes makes it possible to avoid the formation of highly polymerized dextrans possessing α1→3 branching, in particular, which significantly decreases the yield of hydrolysis of dextran by dextranase.

The reaction described in this process enables the production of branched oligodextrans, which represent up to 20% of the products of enzymatic hydrolysis of dextran, to be completely avoided. Isomaltotriose can then be formed, depending on the conditions, by transfer of glucose to isomaltose by the dextransucrase, as well as lesser amounts of other ingredients such as oligosaccharides having a degree of polymerization ranging from 4 to 6, and leucrose.

Another very substantial advantage of the process described is that the starting substrate for the reaction in sucrose, which is cheap and available in large amounts compared with dextran, a relatively expensive product even when of low purity.

The amount of fructose produced represents approximately half the initial sucrose, and constitutes a useful product whose value can be exploited separately.

Hence, the process advantageously comprises the additional stage which consists in separating most of the fructose from the aqueous solution obtained. This separation may be conveniently accomplished by passing the aqueous solution through a column packed with cation exchange resin in the $Ca^{++}$ form, exploiting the property, knon per se, of the affinity of such a resin for fructose.

The temperature of the enzymatic treatment is between 0° and 50° C., preferably between 15° and 35° C., and most especially between 25° and 30° C. to favour the production of isomaltose.

The pH must be maintained in the range from 4.5 to 7, for example using a suitable buffer. It is preferable to work at a pH of 5 to 6.

The concentrations of the enzymes are not strictly critical either. At least 0.1 U/ml of each enzyme is required in order to obtain a significant effect. There is no disadvantage in using large amounts of enzymes except that excessively large amounts are uneconomical. As a guide, concentrations from 0.2 to 2 U/ml approximately of dextransucrase and from 0.2 to 5 U/ml approximately of dextranase have generally proved satisfactory.

As regards the concentration of substrate (sucrose), this can range from 10 to 300 g/liter, and preferably from 50 to 200 g/liter. Below 10 g/l, there is a deficiency of substrate. Above 300 g/l, the formation of leucrose becomes considerable. Leucrose is a disaccharide produced by dextransucrase, which transfers the glucosyl residue derived from the sucrose to the free fructose present in the reaction medium. This disaccharide is an undesirable contaminant. Furthermore, the proportion of isomaltotriose increases significantly above 200 g/l.

The invention also relates to the aqueous isomaltose syrup obtained by the process of the invention, as well as any dry extract obtained by an appropriate drying process (lyophilization, spraying, and the like).

The non-limiting examples which follow are given for the purpose of illustrating the invention.

EXAMPLES 1 TO 12

All the enzymatic syntheses were carried out in a 20 millimolar sodium acetate buffer, pH 5.2, at a temperature of 20° C. and for a reaction time of approximately 48 hours. Under these conditions, the conversion of sucrose is complete.

*Leuconostoc mesenteroides* NRRL B 512 F dextransucrase, obtained from Bio Europe, and endodextranase D1508, obtained from SIGMA, were used.

The solution obtained was purified (separation of most of the fructose) by passing it through a column (height: 1 m; diameter: 5 cm; useful volume: 2 liters) packed with cation exchange resin in the $Ca^{++}$ form, registered trademark Duolite C204F, obtained from Duolite, at room temperature. The fructose retained by the column can be isolated and its value exploited separately.

After this purification, the syrup obtained was analysed by high performance liquid chromatography (HPLC) on a Millipore Waters $\mu$ Bondapack C18 column, the eluent used being ultra-pure water.

The working conditions for each example and the results obtained are recorded in the following table:

| EXAMPLES | 1 | 2 | 3 | 4 | 5 | 6 | 7 | 8 | 9 | 10 | 11 | 12 |
|---|---|---|---|---|---|---|---|---|---|---|---|---|
| CONCENTRATION OF SUCROSE g/liter | 50 | 50 | 50 | 50 | 100 | 100 | 100 | 100 | 200 | 200 | 200 | 200 |
| DEXTRANSUCRASE Units/ml | 0.5 | 0.5 | 0.5 | 0.5 | 0.5 | 1 | 1 | 1 | 0.5 | 1 | 1 | 1 |
| DEXTRANASE, Units/ml | 0.5 | 1 | 2 | 4.8 | 0.5 | 1 | 2 | 4 | 0.5 | 1 | 2 | 4 |
| % OF ISOMALTOSE IN THE DRY EXTRACT | 63 | 67 | 40 | 52 | 62 | 56 | 60 | 64 | 60 | 39 | 53 | 55 |
| % OF ISOMALTOTRIOSE IN THE DRY EXTRACT | 16.6 | 6 | trace | 3 | 30 | 33.7 | 29 | 24 | 35.4 | 30.1 | 33.9 | 33.6 |

From the results obtained, it is seen that, when the concentration of the sucrose substrate is increased for similar concentrations of the two enzymes, a fall in the yield of isomaltose and an increase in the yield of isomaltotriose are observed.

The proportion of glucose present in the final product varies according to the working conditions. Although it was not measured directly, it represents essentially the difference between 100% and the sum of the percentages shown for isomaltose and isomaltotriose, the other constituents possibly present occurring only in very small amounts. As regards the residual fructose content, it may be estimated at 2–3% by weight of the dry extract.

EXAMPLES 13 TO 15

A second series of experiments was carried out using a reaction temperature of 30° C., the other conditions being similar to those described for Examples 1–12.

The following table summarizes the data and results of these experiments.

| EXAMPLES | 13 | 14 | 15 |
|---|---|---|---|
| SUCROSE, g/l | 50 | 100 | 200 |
| DEXTRANSUCRASE U/ml | 1 | 1 | 1 |
| DEXTRANASE, U/ml | 1 | 1 | 1 |
| % OF ISOMALTOSE | 80 | 70 | 65 |
| % OF ISOMALTOTRIOSE | 0 | 12 | 31 |
| GLUCOSE, LEUCROSE, | 20 | 18 | 4 |
| OLIGOSACCHARIDES (traces) | | | |

It is seen from these results that raising the temperature to 30° C. has a beneficial effect, especially for the relatively low concentrations of sucrose. This is probably due to a greater extent of hydrolysis of the isomaltotriose.

It is self-evident that the embodiments described are only examples and that they could be modified, in particular by substitution of equivalent techniques, without thereby departing from the scope of the invention.

We claim:

1. A process for preparing an aqueous syrup, the dry extract of which includes a high content of isomaltose, fructose and glucose as the main constituents, which comprises treating an aqueous solution of sucrose with a mixture of the enzyme in an amount of 0.2 to 2 units per milliliter of said solution of dextransucrase and 0.2 to 5 units per milliliter of said solution of dextranase at a temperature of between 0° and 50° C. and at a pH in the range from 4.5 to 7, so as to obtain said aqueous syrup the dry extract of which includes isomaltose in a proportion of from 39–80%, fructose, and glucose.

2. A process according to claim 1, in which the temperature of the aqueous solution of sucrose with a mixture of the enzymes dextransucrase and dextranase is within the range from about 15° to 35° C.

3. A process according to claim 2, in which the temperature of the aqueous solution of sucrose with a mixture of the enzymes dextransucrase and dextranase is within the range from 25° to 30° C.

4. A process according to claim 1, in which the process time is between 1 and 200 hours.

5. A process according to claim 4, in which the process time is between about 20 and 80 hours.

6. A process according to claim 1, in which the aqueous solution of sucrose with a mixture of the enzymes dextransucrase and dextranase is at a pH from 5 to 6.

7. A process according to claim 1, in which the concentration of sucrose in the initial aqueous solution is between 10 and 300 grams per liter.

8. A process according to claim 7, in which the said concentration is within the range from 50 to 200 grams per liter.

9. A process according to claim 1, wherein said dry extract further comprises isomaltotriose.

10. A process according to claim 1 which comprises the additional step of separating most of the fructose from the aqueous syrup by passing said syrup through a column packed with cation exchanged resin in the $Ca^{++}$ form.

* * * * *